(12) United States Patent
Iwama et al.

(10) Patent No.: US 11,399,799 B2
(45) Date of Patent: Aug. 2, 2022

(54) ULTRASOUND DIAGNOSTIC APPARATUS AND ULTRASOUND PROBE

(71) Applicant: Canon Medical Systems Corporation, Otawara (JP)

(72) Inventors: Nobuyuki Iwama, Nasushiobara (JP);
Shuta Fujiwara, Nasushiobara (JP);
Isao Uchiumi, Nasushiobara (JP);
Hiroyuki Shibanuma, Yaita (JP);
Wataru Kameishi, Nasushiobara (JP);
Yuji Kuwana, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 477 days.

(21) Appl. No.: 16/388,247

(22) Filed: Apr. 18, 2019

(65) Prior Publication Data
US 2019/0321003 A1 Oct. 24, 2019

(30) Foreign Application Priority Data

Apr. 20, 2018 (JP) .............................. JP2018-081197
Apr. 17, 2019 (JP) ................................. 2019-078449

(51) Int. Cl.
| | |
|---|---|
| *A61B 8/00* | (2006.01) |
| *A61B 8/08* | (2006.01) |
| *A61B 8/14* | (2006.01) |
| *A61B 8/15* | (2006.01) |
| *G01S 15/89* | (2006.01) |

(52) U.S. Cl.
CPC .............. *A61B 8/4444* (2013.01); *A61B 8/14* (2013.01); *A61B 8/5246* (2013.01); *A61B 8/54* (2013.01); *A61B 8/15* (2013.01); *A61B 8/463* (2013.01); *A61B 8/5269* (2013.01); *G01S 15/8915* (2013.01)

(58) Field of Classification Search
CPC ..... A61B 8/4405; A61B 8/4411; A61B 8/585; A61B 8/4438
See application file for complete search history.

(56) References Cited

U.S. PATENT DOCUMENTS

| | | | | |
|---|---|---|---|---|
| 2004/0002435 | A1* | 1/2004 | Petersen ............... | B06B 1/0622 510/314 |
| 2005/0203404 | A1* | 9/2005 | Freiburger ............ | G01S 7/5208 600/453 |
| 2008/0110261 | A1* | 5/2008 | Randall ................. | G01S 7/5208 73/592 |
| 2009/0069690 | A1* | 3/2009 | Shin ...................... | A61B 8/4405 600/459 |

(Continued)

FOREIGN PATENT DOCUMENTS

JP 2012-183136 9/2012

*Primary Examiner* — Colin T. Sakamoto
(74) *Attorney, Agent, or Firm* — Oblon, McClelland, Maier & Neustadt, L.L.P.

(57) ABSTRACT

According to one embodiment, an ultrasound diagnostic apparatus includes a plurality of probe ports and processing circuitry. An ultrasound probe including transmission circuitry to drive transducers that generate ultrasound is connectible to each of the plurality of probe ports. The processing circuitry generates a control signal for the transmission circuitry or a drive signal to drive the transmission circuitry, according to a position of one of the probe ports to which the ultrasound probe is connected.

8 Claims, 11 Drawing Sheets

(56) References Cited

U.S. PATENT DOCUMENTS

| | | | |
|---|---|---|---|
| 2014/0171802 A1* | 6/2014 | Kuroiwa | A61B 8/4411 |
| | | | 600/459 |
| 2016/0238563 A1* | 8/2016 | Lee | A61B 8/4411 |
| 2017/0071570 A1* | 3/2017 | Jumatsu | A61B 6/467 |
| 2017/0150944 A1* | 6/2017 | Kim | A61B 8/4433 |

* cited by examiner

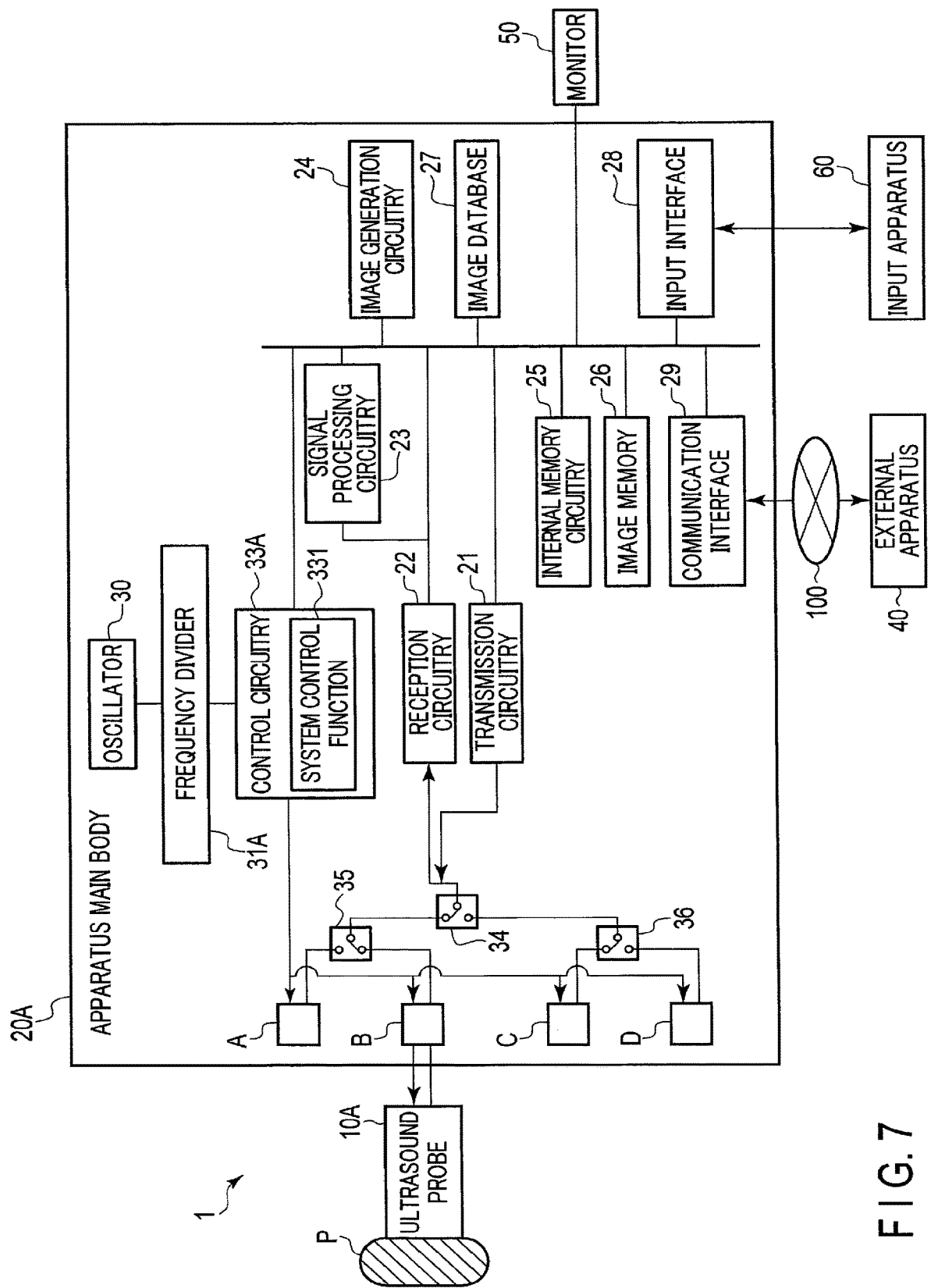
F I G. 7

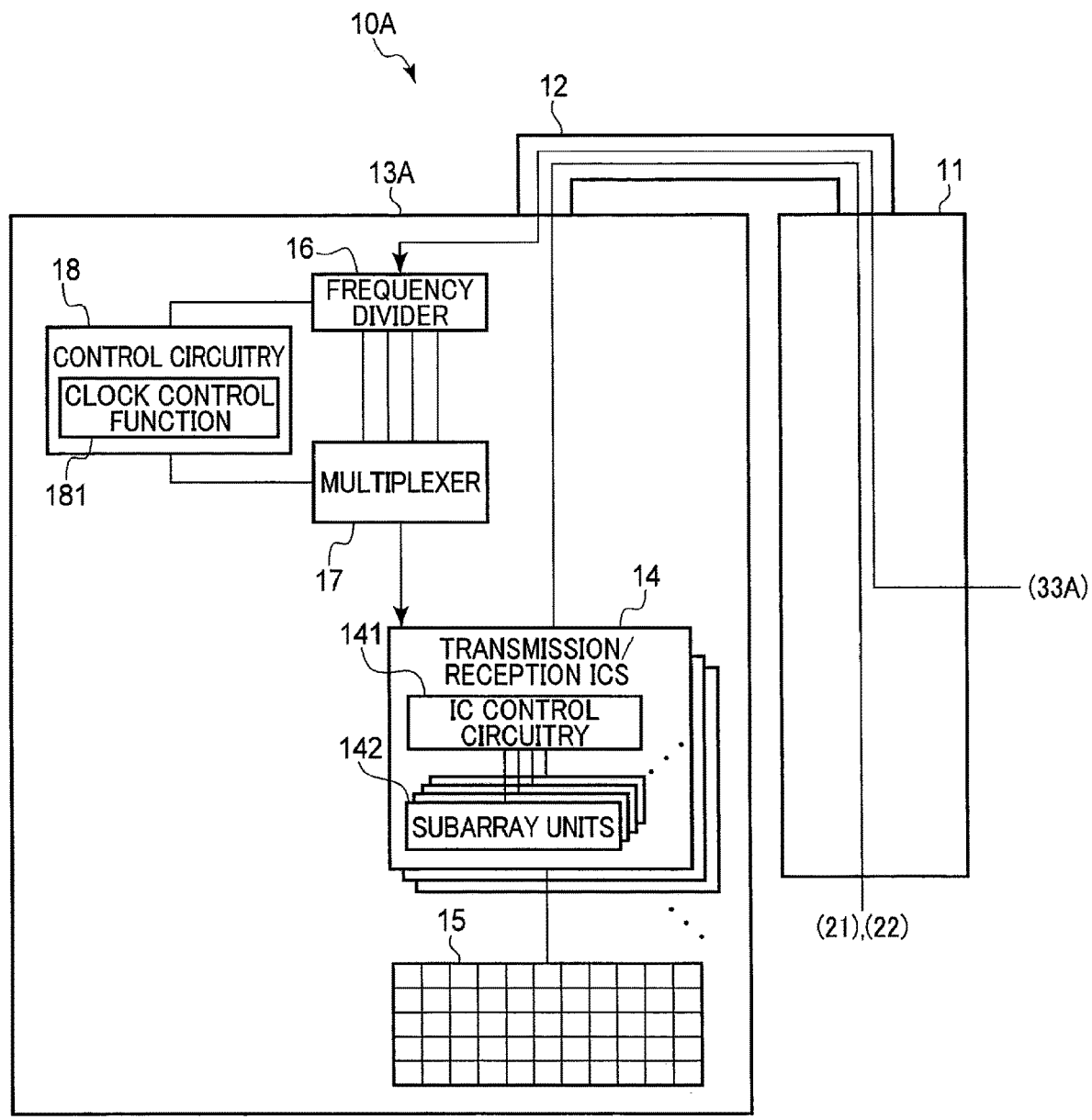
F I G. 8

ULTRASOUND DIAGNOSTIC APPARATUS AND ULTRASOUND PROBE

CROSS-REFERENCE TO RELATED APPLICATIONS

This application is based upon and claims the benefit of priority from the prior Japanese Patent Applications No. 2018-081197, filed Apr. 20, 2018 and No. 2019-78449, filed Apr. 17, 2019, the entire contents of both of which are incorporated herein by reference.

FIELD

Embodiments described herein relate generally to an ultrasound diagnostic apparatus and an ultrasound probe.

BACKGROUND

Some ultrasound probes include built-in transmission circuitry for driving a plurality of ultrasound transducers arranged in an array. In such an ultrasound probe, based on a supply timing of control signals (clock signals), that controls a driving timing of drive signals (transmission pulses) that drives the transmission circuitry, to the transmission circuitry, a depth of a transmission focus is determined. It is thereby possible for the ultrasound probe to form a two-dimensional or three-dimensional transmission beam by changing a position of the transmission focus for every repeated transmission.

Diagnosis with an ultrasound diagnostic apparatus needs to be performed by switching between a plurality of ultrasound probes according to the site to be diagnosed. Accordingly, diagnosis with an ultrasound diagnostic apparatus is performed by changing the probe port to be used with a switch, etc., while keeping a plurality of ultrasound probes connected to the respective probe ports provided in an apparatus main body of the ultrasound diagnostic apparatus, without removing the ultrasound probes.

At this time, to transmit signals of a plurality of transmission and reception channels, large probe ports with 200 to 400 pins, for example, are used as the probe ports between the ultrasound probes and the apparatus main body of the ultrasound diagnostic apparatus, to which the ultrasound probes are connected. If, for example, four probe ports are arranged on a front surface, a side surface, etc. of the apparatus main body so as not to mechanically interfere with each other, the longest distance between the connectors may reach 50 cm.

When control signals are transmitted to the probe ports from a predetermined position of the apparatus main body, a difference in transmission delay occurs between the probe port closest to the output end from which the control signals are output to the probe port most distant therefrom, on the order of a few nanoseconds to five nanoseconds. A difference in transmission delay also occurs in drive signals, as in the control signals, according to the distance between the output end from which the drive signals are output to the probe ports. At this time, variation among the probe ports occurs in delay difference between the drive signal and the control signal.

BRIEF DESCRIPTION OF THE DRAWINGS

FIG. 7 is a diagram showing a configuration of an ultrasound diagnostic apparatus according to a second embodiment.

FIG. 8 is a block diagram showing a configuration of an ultrasound probe according to the second embodiment.

DETAILED DESCRIPTION

In general, according to one embodiment, an ultrasound diagnostic apparatus includes a plurality of probe ports and processing circuitry. An ultrasound probe including transmission circuitry to drive transducers that generate ultrasound is connectible to each of the plurality of probe ports. The processing circuitry generates a control signal for the transmission circuitry or a drive signal to drive the transmission circuitry, according to a position of one of the probe ports to which the ultrasound probe is connected.

Embodiments will be described below with reference to the accompanying drawings.

First Embodiment

An ultrasound diagnostic apparatus 1 according to the first embodiment will be described with reference to the block diagram of FIG. 1.

Figure 1:
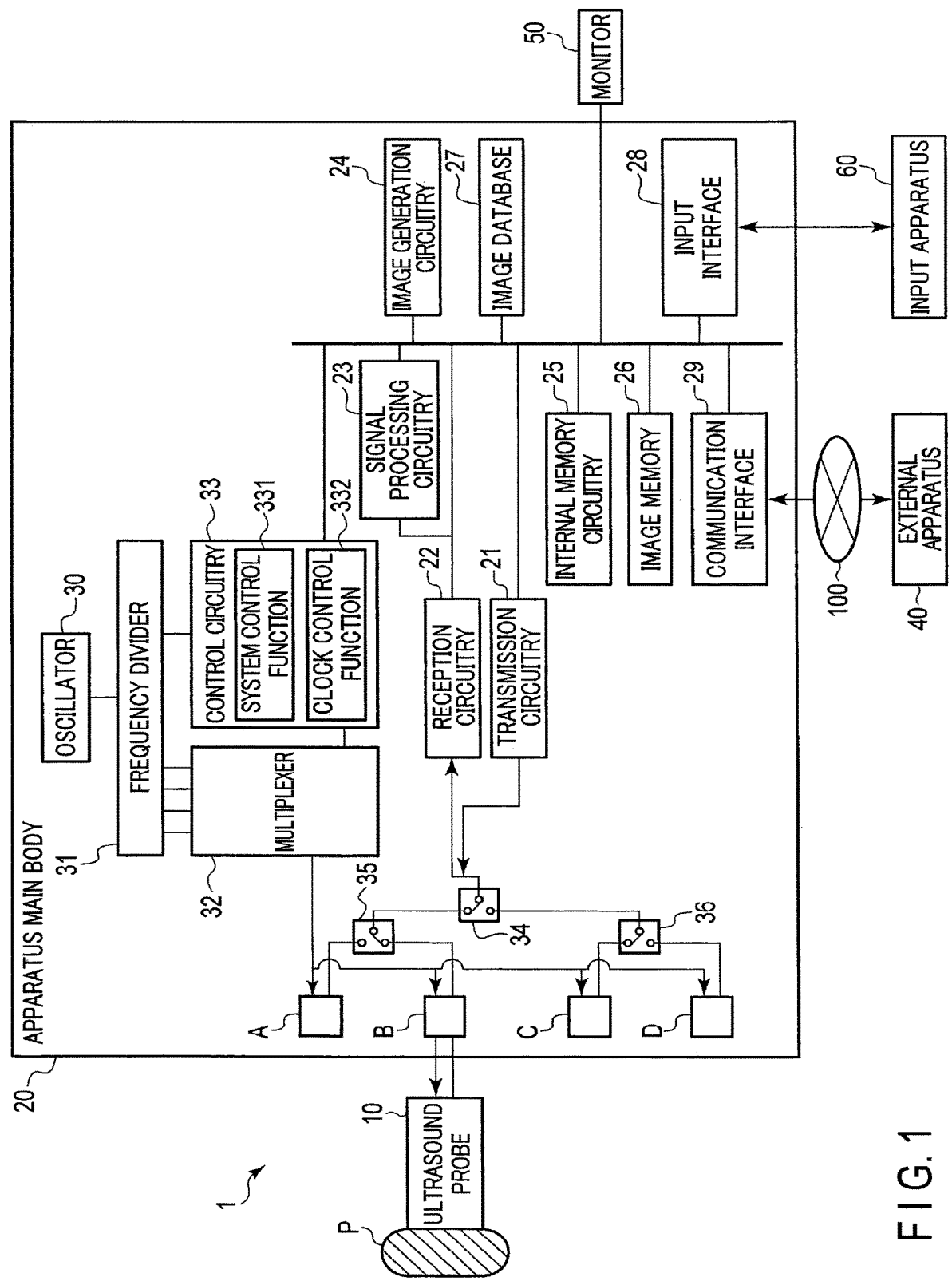
FIG. 1 is a diagram showing a configuration of an ultrasound diagnostic apparatus according to a first embodiment.

FIG. 1 is a block diagram showing a configuration example of an ultrasound diagnostic apparatus 1 according to the first embodiment. As shown in FIG. 1, the ultrasound diagnostic apparatus 1 includes an ultrasound probe 10 and an apparatus main body 20. The apparatus main body 20 is connected to an external apparatus 40 via a network 100. The apparatus main body 20 is connected to a monitor 50 and an input apparatus 60.

The ultrasound probe 10 includes, for example, a plurality of ultrasound transducers (hereinafter also simply referred to as "elements"), a matching layer provided on the elements, and a backing material that prevents the ultrasound from propagating backward from the elements. The ultrasound probe 10 is detachably connected to the apparatus main body 20. The ultrasound probe 10 according to the first embodiment is a two-dimensional array probe in which a plurality of ultrasound transducers are aligned along, for example, a first element alignment direction (elevation direction) and a second element alignment direction (azimuth direction). Details of the ultrasound probe 10 will be described later.

The apparatus main body 20 shown in FIG. 1 is an apparatus that generates an ultrasound image based on a reflected wave signal received by the ultrasound probe 10. As shown in FIG. 1, the apparatus main body 20 includes transmission circuitry 21, reception circuitry 22, signal processing circuitry 23, image generation circuitry 24, internal memory circuitry 25, an image memory (cine memory) 26, an image database 27, an input interface 28, a communication interface 29, an oscillator 30, a frequency divider 31, a multiplexer 32, control circuitry 33, a switch 34, a switch 35, a switch 36, a probe port A, a probe port B, a probe port C, and a probe port D.

The transmission circuitry 21 is a processor that supplies a drive signal (transmission pulse) to the ultrasound probe 10 every predetermined cycle, under the control of the control circuitry 33. The transmission circuitry 21 supplies drive signals to a plurality of ultrasound transducers included in the ultrasound probe 10 via a plurality of channels. Here, "channel" refers to a path included in the transmission circuitry 21 via which a drive signal is generated, or a path via which a drive signal is transmitted from the apparatus main body 20 to the ultrasound probe 10. The transmission circuitry 21 includes, for each channel, a circuitry group for generating drive signals. The transmission circuitry 21 includes, for example, a trigger generation circuit, a delay circuit, and a pulse circuit, for each channel. The trigger generation circuitry repeatedly generates rate pulses for forming transmission ultrasound at a rate frequency based on a clock signal supplied from the control circuitry 33. The delay circuitry provides each rate pulse generated by the trigger generation circuitry with a transmission delay time for each element, which is necessary for converging the ultrasound generated by the ultrasound probe 10 in a beam form and determining a transmission directivity. The pulse circuitry generates a drive signal at a timing based on the rate pulse, and supplies the generated drive signal to the ultrasound probe 10. By varying the transmission delay time provided to each rate pulse by the delay circuit, the transmission direction from the element surface can be discretionarily adjusted. The transmission delay time is calculated by a system control function 331 of the control circuitry 33, which will be described later.

The transmission circuitry 21 changes the number of channels to be driven according to the type of the probe connected to the apparatus main body 20, under the control of the control circuitry 33.

The transmission circuitry 21 routes a drive signal generated by the pulse circuitry through the switch 34 and the switch 35 or 36, and supplies the drive signal to the ultrasound probe 10. By the routing through the switch 34 and the switch 35 or 36 for length matching, it is possible to make the distance from the transmission circuitry 21 to the probe port A, the probe port B, the probe port C, and the probe port D substantially equal.

The reception circuitry 22 is a processor that performs various processes on a reflected wave signal received by the ultrasound probe 10 and generates a reception signal. The reception circuitry 22 includes, for example, an amplifier circuit, an analog-to-digital (A/D) converter, a reception delay circuit, an adder, etc., for each channel. The amplifier circuitry performs a gain correction process by amplifying the reflected wave signal received by the ultrasound probe 10 for each channel. The A/D converter converts the gain-corrected reflected wave signal into a digital signal. The reception delay circuitry provides the digital signal with a delay time necessary for determining a reception directivity. The adder sums a plurality of digital signals each provided with a delay time. By the summation process of the adder, a reception signal enhanced with a component reflected from a direction corresponding to the reception directivity is generated.

The signal processing circuitry 23 is a processor that performs various types of signal processing on a reception signal received from the reception circuitry 22. The signal processing circuitry 23 performs an envelope detection process, a logarithmic amplification process, etc. on the reception signal received from the reception circuitry 22, and generates data (B-mode data) that expresses the signal intensity in brightness. The generated B-mode data is stored in a raw data memory (not shown in the drawings) as two-dimensional B-mode raw data on an ultrasound scan line.

The signal processing circuitry 23 performs a frequency analysis on the reception signal received from the reception circuitry 22 to extract a blood flow signal, and generates data (Doppler data) obtained by extracting a number of items of information from the blood flow signal, such as an average speed, dispersion, and power. The generated Doppler data is stored in a raw data memory (not shown in the drawings) as two-dimensional Doppler raw data on an ultrasound scan line.

The signal processing circuitry 23 extracts a blood flow signal from the reception signal received from the reception circuitry 22, and generates Doppler spectrum image data representing a Doppler spectrum image indicative of a Doppler waveform from the extracted blood flow signal. A Doppler waveform is a waveform on which blood flow velocities in an area set as a site to be observed are plotted along the timeline. That is, a Doppler waveform represents changes in blood flow velocity over time.

The image generation circuitry 24 is a processor capable of generating various types of ultrasound image data based on data generated by the signal processing circuitry 23.

The image generation circuitry 24 generates B-mode image data based on the B-mode raw data stored in the raw data memory. A B-mode image based on the B-mode image data shows, for example, a form of a biological structure in a subject P. The B-mode image data has a pixel value (brightness value) reflecting, for example, characteristics of the ultrasound probe, such as convergence of sound waves, and sound-field characteristics of an ultrasonic beam (e.g., a transmitted/received beam). For example, B-mode image data has relatively higher brightness in the vicinity of the focus of ultrasound in the scanned area than in an out-of-focus portion.

The image generation circuitry 24 generates Doppler image data, which represents information on a moving object on the basis of the Doppler raw data stored in the raw data memory. The Doppler image data is one of velocity image data, dispersion image data, and power image data, or image data obtained by a combination thereof.

The image generation circuitry 24 converts (scan-converts) a scan line signal sequence of ultrasound scanning into, for example, a scan line signal sequence in a video format representatively used by television, etc. to generate ultrasound image data for display. Specifically, the image generation circuitry 24 performs a coordinate conversion according to the form of ultrasound scanning performed by the ultrasound probe 10 to generate ultrasound image data for display. An ultrasound image based on the ultrasound image data for display is displayed on, for example, the monitor 50. As the monitor 50, for example, a CRT display, a liquid crystal display, an organic EL display, an LED display, a plasma display, or any other display known in the relevant technical field may be suitably used. The monitor 50 may be a touch panel with an input function for allowing a touch operation to be performed.

The image generation circuitry 24 may perform various processes, such as dynamic range, brightness, contrast, γ curve corrections, and an RGB conversion, on the generated various types of ultrasound image data. The image generation circuitry 24 may add supplementary information, such as textual information of various parameters, a scale, or a body mark, etc. to the generated various types of ultrasound image data.

The image generation circuitry 24 may generate a user interface, such as a graphical user interface (GUI) for allowing an operator (e.g., a laboratory technician, an operator, etc.) to enter various commands via the input interface 28, and display the GUI on the monitor 50.

The internal memory circuitry 25 includes, for example, a magnetic or optical storage medium, or a processor-readable storage medium such as a semiconductor memory. The internal memory circuitry 25 stores, for example, a control program relating to a method for setting an amount of delay according to the first embodiment, a control program for realizing transmission and reception of the ultrasound, a control program for performing image processing, and a control program for performing display processing. The internal memory circuitry 25 also stores diagnostic information (e.g., a patient's ID, a doctor's observation, etc.), a diagnostic protocol, a body mark generation program, and a data group such as a conversion table in which the range of color data used for imaging is preset for each site to be diagnosed. The internal memory circuitry 25 may store anatomical illustrations, for example, an atlas, relating to the structures of internal organs in the body.

The internal memory circuitry 25 stores, in accordance with a memory operation input via the input interface 28, two-dimensional image data, volume data, and rendering image data generated at the image generation circuitry 24. The internal memory circuitry 25 may store the two-dimensional image data, the volume data, and the rendering image data generated at the image generation circuitry 24 together with the operation order and operation time, in accordance with a memory operation that is input via the input interface 28. The internal memory circuitry 25 can transfer the stored data to an external device via the communication interface 29.

The internal memory circuitry 25 stores control information. The control information is, for example, information for controlling a clock signal as a control signal. In the control information, a plurality of probe ports included in the apparatus main body 20 and a plurality of clock signals having different phases are associated with each other in accordance with the positions of the probe ports. In this correspondence relation, a probe port and a clock signal are associated in such a manner that a delay difference generated between a drive signal input to in-probe transmission circuitry 1421 in the ultrasound probe 10 connected to the probe port and the clock signal as a control signal that is input to the in-probe transmission circuitry 1421 falls within a predetermined range of values. The predetermined range is set to be sufficiently small in length, for example, from ⅛ to ¼ of one clock of a clock signal. The control information is set at a predetermined timing, for example, at the time of installation of the ultrasound diagnostic apparatus 1, or at the time of maintenance. The control information may be updated as necessary.

The image memory 26 includes, for example, a magnetic or optical storage medium, or a processor-readable storage medium such as a semiconductor memory. The image memory 26 stores image data items corresponding to a plurality of frames immediately before a freeze operation input via the input interface 28. The image data stored in the image memory 26 is, for example, continuously displayed (cine-displayed).

The image database 27 stores image data transferred from the external apparatus 40. For example, the image database 27 receives historic medical image data related to a particular patient acquired by the past diagnosis and stored in the external apparatus 40, and stores the received medical image data. The historic medical image data includes ultrasound image data, computed tomography (CT) image data, MR image data, positron-emission tomography (PET-CT) image data, PET-MR image data, and X-ray image data.

The image database 27 may store desired image data by reading image data stored in a storage medium such as an MO, a CD-R and a DVD.

The input interface 28 receives various types of instructions from a user via the input apparatus 60. The input apparatus 60 is, for example, a mouse, a keyboard, a panel switch, a slider switch, a trackball, a rotary encoder, an operation panel, or a touch command screen (TCS). The input interface 28 is connected to the control circuitry 33 via, for example, a bus, converts an operation instruction that is input by the operator into an electrical signal, and outputs the electrical signal to the control circuitry 33. In the present specification, the input interface 28 is not limited to those connected to physical operation components such as a mouse, a keyboard, etc. Examples of the input interface 28 may include electric signal processing circuitry which receives, as radio signals, electric signals corresponding to an operation instruction input from an external input device provided independently from the ultrasound diagnostic apparatus 1, and outputs the electric signals to the control circuitry 33. Examples of the input interface 28 may also include an external input device capable of transmitting an operation instruction corresponding to the operator's gesture as radio signals.

The communication interface 29 is connected to the external apparatus 40 via, for example, the network 100, and performs data communication with the external apparatus 40. The external apparatus 40 is, for example, a database of a picture archiving and communication system (PACS), which is a system for managing data of various types of medical images, and a database of an electronic health record system which manages electronic health records accompanied with medical images. The external apparatus 40 is, for example, a medical imaging diagnostic apparatus other than the ultrasound diagnostic apparatus 1 according to the first embodiment, such as an X-ray CT apparatus, a magnetic resonance imaging (MRI) apparatus, a nuclear medicine diagnostic apparatus, or an X-ray diagnostic apparatus. For the standard of the communication with the external apparatus 40, any standard may be used, and examples of such a standard include Digital Imaging and Communications in Medicine (DICOM).

The oscillator 30 supplies a reference clock signal for driving the circuitry included in the apparatus main body 20. The oscillator 30 generates a reference clock signal of, for example, 320 MHz, and supplies the generated reference clock signal to the frequency divider 31.

The frequency divider 31 frequency-divides the reference clock signal supplied from the oscillator 30, and supplies the frequency-divided clock signal to the control circuitry 33. Specifically, the frequency divider 31 frequency-divides, for example, a reference clock signal of 320 MHz supplied from the oscillator 30 by two, and supplies a clock signal of 160 MHz generated by the frequency division by 2 to the control circuitry 33.

The frequency divider 31 generates a plurality of clock signals with different phases based on the reference clock signal supplied from the oscillator 30, and supplies the generated clock signals to the multiplexer 32. Specifically, the frequency divider 31 frequency-divides, for example, a reference clock signal of 320 MHz supplied from the oscillator 30 by 4, and generates four clock signals of 80 MHz with different phases. The frequency divider 31 supplies the generated four clock signals to the multiplexer 32.

Figure 2:
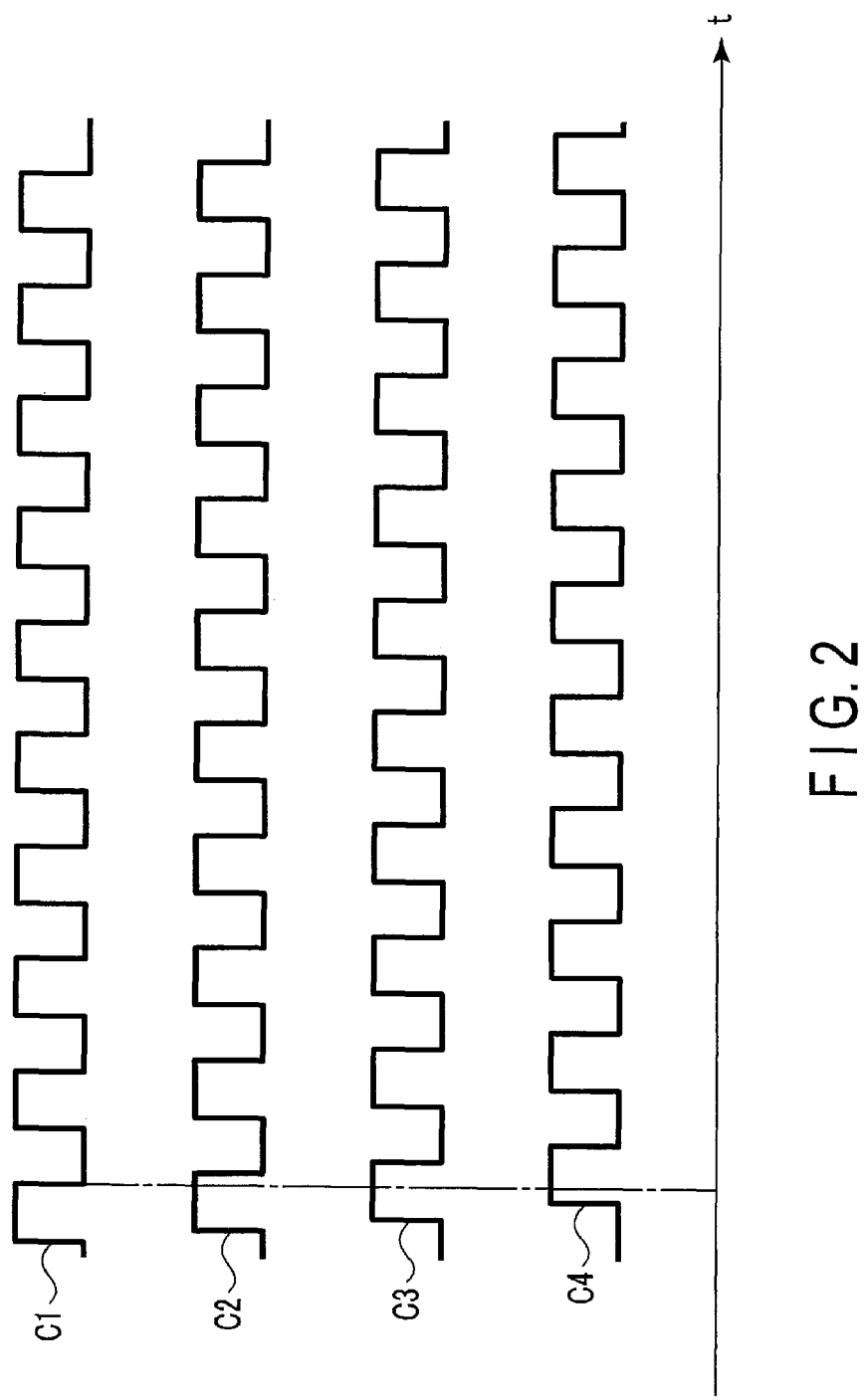
FIG. 2 is a diagram showing clock signals generated in a frequency divider shown in FIG. 1.

FIG. 2 is a schematic diagram showing an example of four clock signals with different phases generated in the frequency divider 31 shown in FIG. 1. Clock signals C1 to C4 with four types of phases, as shown in FIG. 2, are supplied to the multiplexer 32.

Of the four clock signals supplied from the frequency divider 31, the multiplexer 32 extracts one designated clock signal as a control signal to be supplied to the probe port A, B, C, or D, under the control of the control circuitry 33. Thereby, control signals corresponding to the respective probe ports are generated. The multiplexer 32 supplies a generated clock signal to the probe port A, B, C, or D.

The control circuitry 33 is a processor that functions as, for example, the center of the ultrasound diagnostic apparatus 1. The control circuitry 33 executes the control program stored in the internal memory circuitry 25, and realizes the function corresponding to the program. Specifically, the control circuitry 33 includes a system control function 331 and a clock control function 332.

The system control function 331 is a function of controlling basic operations of the ultrasound diagnostic apparatus 1, such as input and output, and transmission and reception of the ultrasound. When the system control function 331 is executed, the control circuitry 33 receives a clock signal output from, for example, the frequency divider 31. The control circuitry 33 performs various types of control, using a clock based on the received clock signal as a reference clock. For example, the control circuitry 33 controls the timing of transmission, and transfers setting data to the circuitry, using a clock based on a clock signal of 160 MHz supplied from the frequency divider 31 as a reference clock. Specifically, the control circuitry 33 supplies, for example, a clock signal of 160 MHz to the transmission circuitry 21.

The control circuitry 33 computes delay control data (delay data) on a delay time (a transmission delay time and a reception delay time) set in each of the ultrasound transducers at the time of transmission and reception of the ultrasound. The control circuitry 33 supplies the computed delay data to the ultrasound probe 10, together with the setting information.

The ultrasound diagnostic apparatus 1 according to the first embodiment performs the delay data computation process by assigning the process to both the ultrasound probe 10 and the apparatus main body 20. That is, a part of the delay data to be set is computed by the ultrasound probe 10, and the remaining part of the delay data to be configured is computed by the apparatus main body 20.

The control circuitry 33 updates the contents of the control information stored in the internal memory circuitry 25 on the basis of, for example, the information input via the input interface 28. It is thereby possible to cope with the change in arrangement or number of the probe ports caused by a design change, for example, of the ultrasound diagnostic apparatus. Moreover, it is possible to suppress variation, among the probe ports, in delay difference between a drive signal that drives the transmission circuitry 14 provided in the ultrasound probe 10 and a control signal that controls the driving timing of the transmission circuitry 14, even though the position of the oscillation source of clock signals may vary depending on the model of the ultrasound diagnostic apparatus.

The clock control function 332 is a function of generating control signals for in-probe transmission circuitry 1421 included in the ultrasound probe 10, which will be described later, according to the position of the probe port to which the ultrasound probe 10 is connected. When the clock control function 332 is executed, the control circuitry 33 reads control information from the internal memory circuitry 25. The control circuitry 33 selects a clock signal to be selected on the basis of the probe port to which the ultrasound probe 10 is connected, and the correspondence relation represented by the control information. The control circuitry 33 gives an instruction to the multiplexer 32 to extract the selected clock signal from, for example, four clock signals supplied from the frequency divider 31. Thereby, the selected clock signal is extracted in the multiplexer 32, and the extracted clock signal is supplied to the probe port as a control signal. The control information may be stored in a flash memory, for example, implemented on the control circuitry 33, and read at the time of activation of the apparatus. The control information may be updated as necessary via, for example, the input interface 28.

The functions executed by the control circuitry 33 may be incorporated as control programs; alternatively, dedicated hardware circuitry capable of performing the respective functions may be incorporated in the control circuitry 33 itself or the apparatus main body 20.

The control circuitry 33 may be realized by an application-specific integrated circuit (ASIC), a field-programmable gate array (FPGA), a complex programmable logic device (CPLD), or a simple programmable logic device (SPLD), into which such dedicated hardware circuitry is incorporated.

The probe ports A, B, C, and D are slots for allowing the ultrasound probe 10 to be detachably connected to, for example, the apparatus main body 20. FIG. 1 shows the ultrasound probe 10 connected only to the probe port B; however, let us assume that, in the first embodiment, ultrasound probes (not shown in the drawings) are connected to the respective probe ports A, C, and D as well. FIG. 1 shows an example in which the probe port B is designated via the input interface 28, and the ultrasound probe 10 connected to the probe port B can be used by switching between the switches 34, 35, and 36. At this time, the ultrasound diagnostic apparatus 1 allows the apparatus main body 20 and the ultrasound probe 10 to transmit and receive various types of data on ultrasound scanning to and from each other.

Let us assume that, in the first embodiment, the probe ports are arranged in such a manner that the distance from the multiplexer 32 to each probe port increases in the order of the probe ports A, B, C, and D. At this time, the propagation delay time taken for the clock signal output from the multiplexer 32 to be propagated increases in the order of the probe ports A, B, C, and D. That is, a clock signal output from the multiplexer 32 reaches the probe port A fastest, and reaches the probe ports B, C, and D in this order, later than the probe port A.

Figure 3:
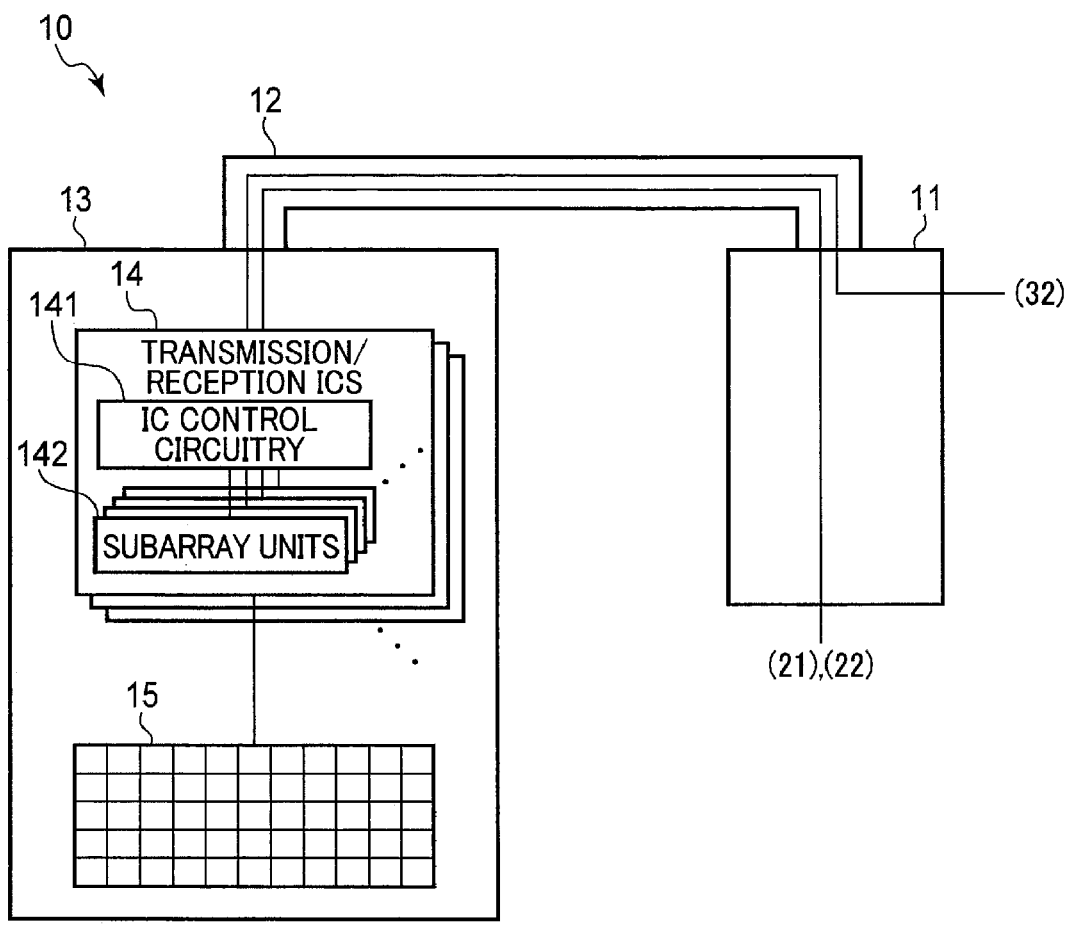
FIG. 3 is a block diagram showing a configuration of an ultrasound probe according to the first embodiment.
Figure 4:
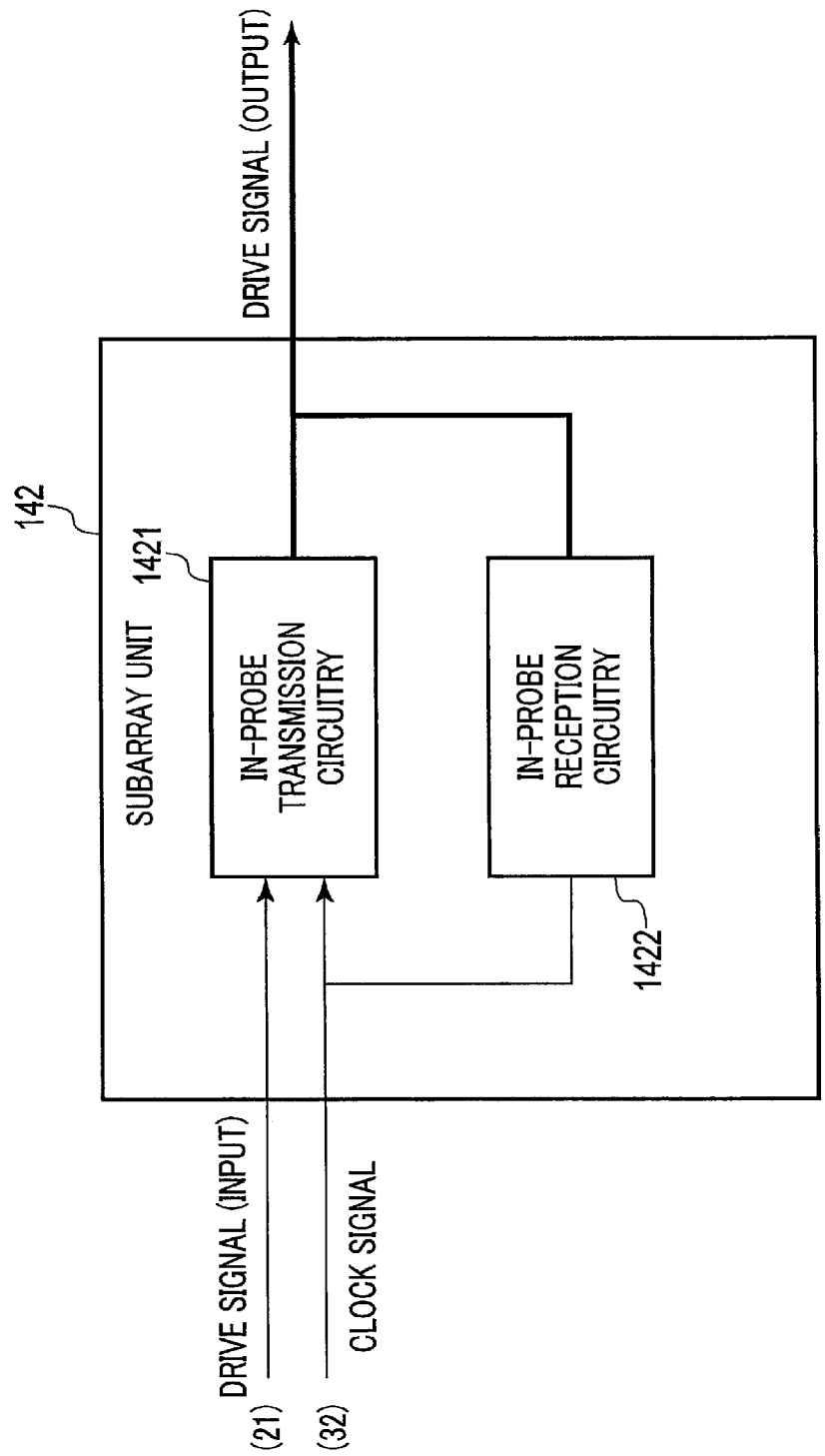
FIG. 4 is a block diagram showing a configuration of a subarray unit according to the first embodiment.

Next, details of the ultrasound probe 10 according to the first embodiment will be described with reference to FIGS. 3 and 4. FIG. 3 is a block diagram showing an example of a configuration of the ultrasound probe 10 according to the first embodiment.

The ultrasound probe 10 includes a connecting member (also referred to as "POD"), a cable 12, and a probe main body 13 (also referred to as "HEAD").

In FIG. 3, the probe main body 13 includes a plurality of transmission and reception ICs 14 and a plurality of ultrasound transducers 15 (also simply referred to as "elements").

Each of the transmission and reception ICs 14 receives, for example, setting information and delay data from the control circuitry 33 of the apparatus main body 20 via a communication control circuitry (not shown in the drawings) included in the connecting member 11 (via a path not shown in the drawings), receives a clock signal from the multiplexer 32, and receives a drive signal from the transmission circuitry 21. At this time, the setting information is information necessary for scanning by the ultrasound probe 10, such as the focus and depth of the ultrasonic beam. The delay data received from the control circuitry 33 is, for example, delay data determined for each of a plurality of elements belonging to a subarray. When using two-dimensional array probe in which a plurality of elements are aligned along a first alignment direction and a second alignment direction, the delay data received from the control circuitry 33 may be delay data determined in units of element strings, with respect to each direction.

Each of the transmission and reception ICs 14 sets amounts of delay of elements for each subarray to be controlled by the transmission and reception IC 14, on the basis of the setting information, the delay data, the clock signal, and the drive signal, and controls transmission and reception of ultrasound at a predetermined timing. Details of the transmission and reception ICs 14 will be described below.

Each of the transmission and reception ICs 14 includes IC control circuitry 141, and a plurality of subarray units 142. The IC control circuitry 141 calculates, for each subarray, amounts of delay of elements belonging to the subarray on the basis of the setting information and the delay data acquired from the control circuitry 33 of the apparatus main body 20, and supplies the calculated amounts of delay to the respective subarray units 142.

Each of the subarray units 142 receives a drive signal from the transmission circuitry 21, a clock signal from the multiplexer 32, and an amount of delay from the IC control circuitry 141. Based on the received drive signal, the clock signal, and the amount of delay, each subarray unit 142 controls the timing of transmission and reception of the ultrasound by elements in a subarray allocated thereto.

The ultrasound transducers 15 transmit ultrasound generated at a timing determined based on control by the transmission and reception IC 14 to a subject P.

When the ultrasonic waves are transmitted from the ultrasound probe 10 to the subject P, the transmitted ultrasonic waves are sequentially reflected off surfaces with non-uniform acoustic impedance in body tissues of the subject P, and the reflected waves are received by the ultrasound transducers 15. The amplitude of the received reflected waves depends on the difference in acoustic impedance of the surfaces with non-uniform acoustic impedance, off which the ultrasonic waves are reflected. In a case where a transmitted ultrasonic pulse is reflected off a surface of a moving object, such as flowing blood or the cardiac wall, the reflected wave is shifted in frequency by the Doppler effect, depending on the velocity component of the moving object with respect to the ultrasound transmission direction. The ultrasound probe 10 receives the reflected waves from the subject P, converts the received reflected waves into an electric signal, and transmits the electric signal to the apparatus main body 20.

Next, details of the subarray units 142 will be described with reference to the block diagram shown in FIG. 4.

Each of the subarray units 142 includes, for example, in-probe transmission circuitry 1421 and in-probe reception circuitry 1422. The in-probe transmission circuitry 1421 and the in-probe reception circuitry 1422 are provided for, for example, each channel.

The in-probe transmission circuitry 1421 receives a drive signal from the transmission circuitry 21, receives a clock signal from the multiplexer 32, and receives an amount of delay from the IC control circuitry 141. The in-probe transmission circuitry 1421 sets an amount of delay of each ultrasound transducer 15 belonging to a subarray, with respect to the drive signal supplied from the transmission circuitry 21. The in-probe transmission circuitry 1421 generates a drive signal for driving the ultrasound transducer 15 at the timing based on the clock signal supplied from the multiplexer 32. The in-probe transmission circuitry 1421 causes the generated drive signal to be delayed by a set amount of delay, and outputs the delayed drive signal to the ultrasound transducer 15 belonging to the subarray.

As an example, the in-probe reception circuitry 1422 receives a reflected wave signal from the ultrasound transducer 15, receives a clock signal from the multiplexer 32, and receives an amount of delay from the IC control circuitry 141. The in-probe reception circuitry 1422 sets an amount of delay in the reception signal based on the reflected wave signal, for each of the ultrasound transducers 15 belonging to a subarray. The in-probe reception circuitry 1422 generates a reception signal based on the reflected wave signal received by the ultrasound transducer 15. The in-probe reception circuitry 1422 causes the generated reception signal to be delayed by an amount of delay set for each ultrasound transducer 15. The delayed reception signal is added by adder circuitry (not shown in the drawings) included in the subarray unit 142, and is supplied to the apparatus main body 20 via the cable 12.

Next, the operation from start of ultrasound scanning until provision of a drive signal and a clock signal to the in-probe transmission circuitry 1421 will be described. In the description that follows, let us assume that ultrasound probes are connected to the respective probe ports A, B, C, and D. The ultrasound probes connected to the respective probe ports A, B, C, and D have configurations similar to that of the ultrasound probe 10 shown in FIG. 3; however, let us assume that their shapes and structures, and some of their functions vary depending on the intended use.

Upon receiving an instruction to start ultrasound scanning via, for example, the input interface 28, the control circuitry 33 included in the apparatus main body 20 executes the clock control function 332 and reads control information from the internal memory circuitry 25. At this time, the control information represents, for example, a correspondence relation between the probe ports A, B, C, and D and four clock signals of 80 MHz with different phases supplied from the frequency divider 31.

In this correspondence relation, the probe ports A, B, C, and D and the four clock signals are associated with each other in such a manner that a drive signal that drives the in-probe transmission circuitry 1421 and a clock signal that controls the driving timing of the in-probe transmission circuitry 1421 circuitry 1421 are substantially synchronized, when observed with, for example, an oscilloscope by the operator.

The control information may be set by, for example, theoretically calculating clock signals that have phases corresponding to the respective probe ports A, B, C, and D, on the basis of the transmission path lengths of the clock signals supplied to the respective probe ports. At this time, the control circuitry 33 measures distances from the multiplexer 32 to the probe ports A, B, C, and D, namely, the transmission path lengths of the clock signals, and associates the clock signals that have phases corresponding to the measured transmission path lengths with the corresponding probe ports.

The control circuitry 33 selects a clock signal with a phase corresponding to the designated probe port, on the basis of the read control information. The control circuitry 33 gives an instruction to the multiplexer 32 to extract the selected clock signal. Thereby, after the ultrasound scanning is started, a clock signal corresponding to the position of the designated probe port is generated in the multiplexer 32. The generated clock signal is supplied to the in-probe transmission circuitry 1421 of a corresponding channel, via the designated probe port.

On the other hand, the control circuitry 33 controls the transmission circuitry 21, generates a drive signal at a timing based on a clock signal of 160 MHz supplied from the frequency divider 31, and supplies the generated drive signal to the in-probe transmission circuitry 1421 of a corresponding channel via the designated probe port.

Upon receiving an instruction to switch to another probe port via, for example, the input interface 28 after the start of ultrasound scanning, the control circuitry 33 selects a clock signal with a phase corresponding to the probe port to which the switch is made, on the basis of the control information read at the time of start of the ultrasound scanning. The control circuitry 33 gives an instruction to the multiplexer 32 to extract the selected clock signal. Thereby, after the switch is made to another port, namely, after the switch is made to the ultrasound probe to be used, a clock signal corresponding to the position of the probe port to which the switch is made is generated in the multiplexer 32. The generated clock signal is supplied to the in-probe transmission circuitry 1421 of the corresponding channel, via the probe port to which the switch is made.

Figure 5:
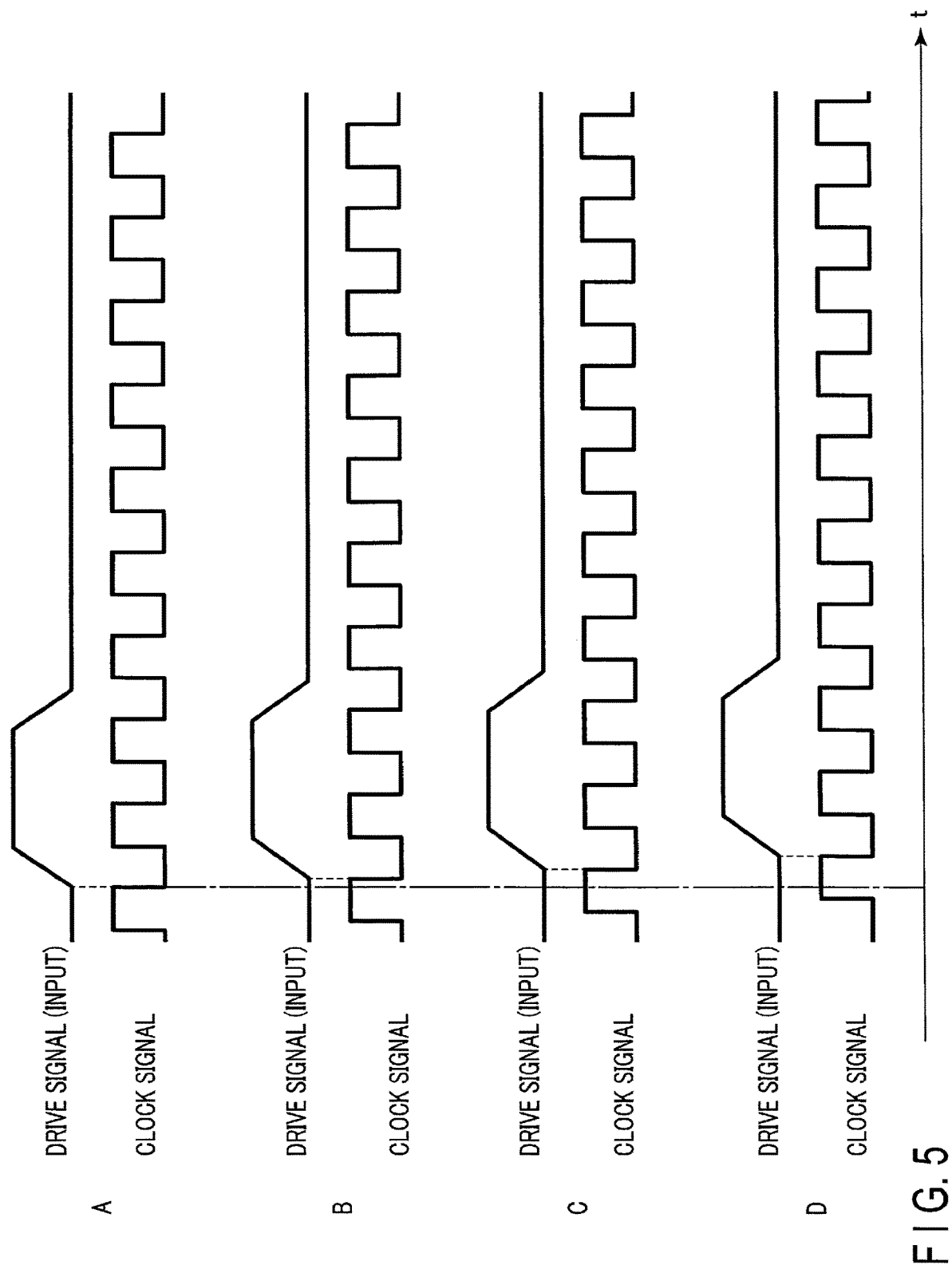
FIG. 5 is a diagram illustrating various types of signals input to in-probe transmission circuitry via probe ports included in the ultrasound diagnostic apparatus according to the first embodiment.

According to the above-described operations, it is possible to perform ultrasound scanning while minimizing a delay difference between a drive signal that drives the in-probe transmission circuitry 1421 provided in the ultrasound probe 10 and a control signal that controls the driving timing of the in-probe transmission circuitry 1421, no matter which of the probe ports is used. FIG. 5 is a diagram illustrating various types of signals input to the in-probe transmission circuitry 1421 via the probe ports included in the ultrasound diagnostic apparatus 1, according to the first embodiment. FIG. 5 shows relations between drive signals input to the in-probe transmission circuitry 1421 via the probe ports A, B, C, and D and clock signals. Let us assume that, in FIG. 5, clock signals that have phases corresponding to the probe ports A, B, C, and D are supplied from the multiplexer 32 by the clock control function 332. At this time, it can be seen, from FIG. 5, that the timing when a drive signal reaches a probe port varies among the probe ports, according to the distance between the transmission circuitry 21 and the probe port. On the other hand, since the probe ports are supplied with clock signals with corresponding phases, the rising edge timing of the drive signal and the ON-to-OFF transition timing of the clock signal are substantially aligned in each of the probe ports. That is, the drive signal and the clock signal are substantially synchronized. This suppresses variation in delay difference between the clock signals supplied from the multiplexer 32 to the in-probe transmission circuitry 1421 via the probe ports A, B, C, and D and the drive signals supplied from the transmission circuitry 21 to the in-probe transmission circuitry 1421 via the probe ports A, B, C, and D.

Figure 6:
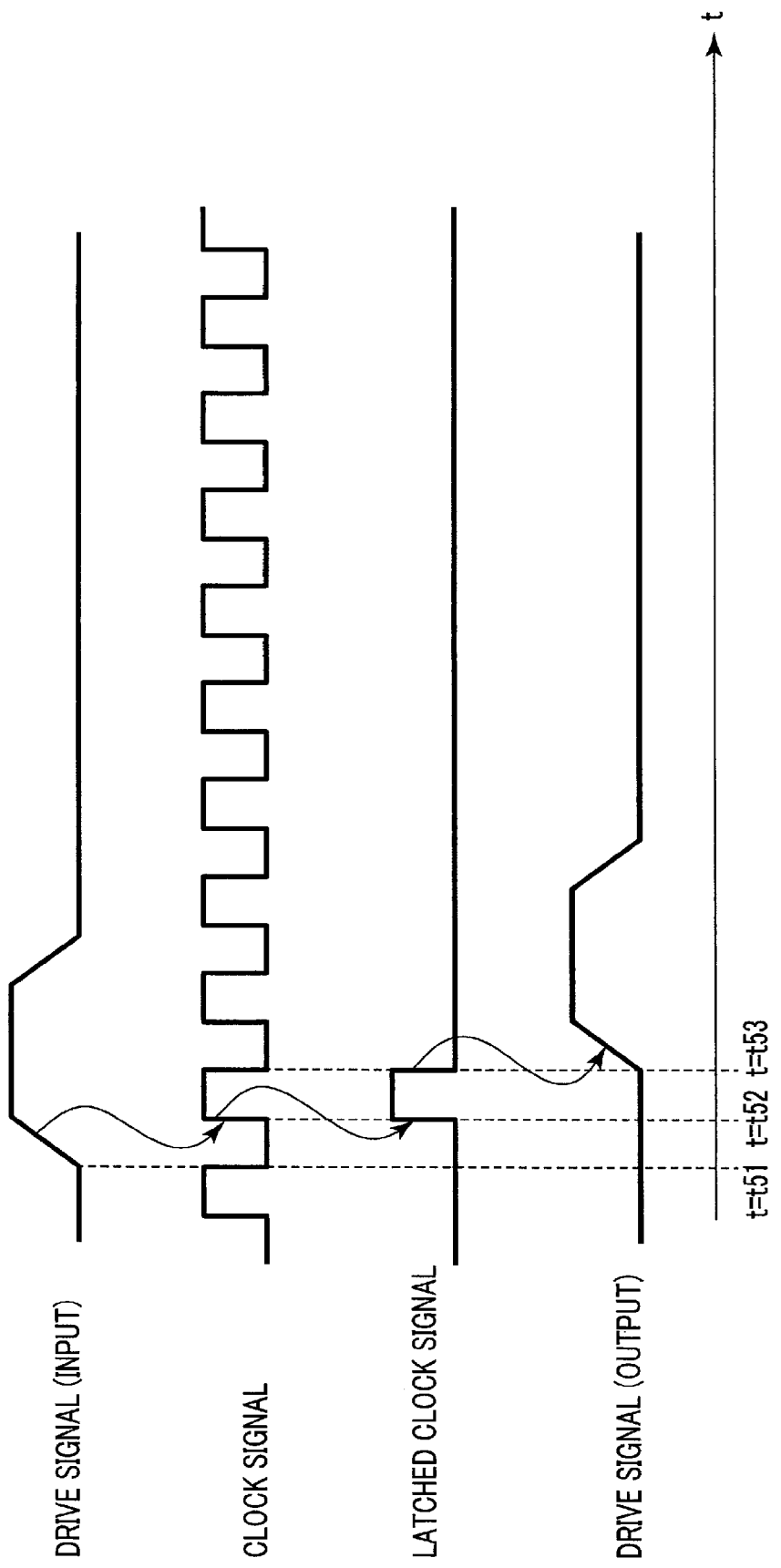
FIG. 6 is a diagram illustrating an output timing of a drive signal output from the in-probe transmission circuitry according to the first embodiment.

Next, the output timing of drive signals output from the in-probe transmission circuitry 1421 according to the first embodiment will be described. In the description that follows, let us assume that the probe port B is designated as a probe port to be used at the time of ultrasound scanning. FIG. 6 is a diagram illustrating an output timing of a drive signal output from the in-probe transmission circuitry 1421 according to the first embodiment. In FIG. 6, since the probe port B is designated, the control circuitry 33 of the apparatus main body 20 selects a clock signal with a phase corresponding to the probe port B.

Specifically, the control circuitry 33 reads control information from the internal memory circuitry 25. The control circuitry 33 selects a clock signal with a phase corresponding to the probe port B, on the basis of the read control information. The control circuitry 33 gives an instruction to the multiplexer 32 to extract the selected clock signal from, for example, four clock signals of 80 MHz with different phases supplied from the frequency divider 31. Thereby, a clock signal corresponding to the position of the probe port B is generated in the multiplexer 32, and is supplied to the probe port B. At this time, as shown in FIG. 6, both the rising edge timing of the transmission pulse represented by the drive signal received by the in-probe transmission circuitry 1421 and the ON-to-OFF transition timing of the clock signal received by the in-probe transmission circuitry 1421 are represented by t=t51.

At timing t=t52 immediately after t=t51, when the clock signal transitions from OFF to ON, the in-probe transmission circuitry 1421 latches the clock signal for one clock. The in-probe transmission circuitry 1421 generates a drive signal for driving the ultrasound transducer 15 in such a manner that the transmission pulse starts to rise at a timing t=t53, when the latched clock signal transitions from ON to OFF. That is, the in-probe transmission circuitry 1421 uses the clock signal of one clock, which occurs after the rising edge of the transmission pulse transmitted from the transmission circuitry 21, as the driving timing. Thereby, a drive signal for driving the ultrasound transducer 15 is generated at a predetermined timing after a drive signal is supplied, regardless of which of the probe ports the ultrasound probe 10 is connected to.

According to the first embodiment, the apparatus main body 20 of the ultrasound diagnostic apparatus 1 includes probe ports A, B, C, and D to which an ultrasound probe 10 including in-probe transmission circuitry 1421 for driving transducers that generate ultrasound can be connected. The control circuitry 33 included in the apparatus main body 20 of the ultrasound diagnostic apparatus 1 generates a clock signal to the in-probe transmission circuitry 1421 provided in the ultrasound probe 10, according to the position of the probe port to which the ultrasound probe 10 is connected.

In a conventional ultrasound diagnostic apparatus in which drive signals that drive ultrasonic transducers are directly transmitted to an ultrasound probe from the transmission circuitry of the apparatus main body, variation among the probe ports occurs in drive signals routed from the substrate of the transmission circuitry; however, the paths of the drive signals substantially match in length among the channels of the probe ports.

In a conventional ultrasound diagnostic apparatus in which transmission and reception circuitry is integrated in an ultrasound probe and the ultrasound is transmitted and received based on a synchronization signal of an apparatus main body, variation in time phase between a drive signal and a clock signal, namely, variation in synchronization timing between a drive signal and a clock signal may cause variation in transmission phase and reception phase among channels, resulting in defocus, or may cause variation in transmission phase and reception phase among transmission and reception rates, resulting in an artifact (e.g., noise generated in color Doppler mode).

According to the ultrasound diagnostic apparatus 1 of the first embodiment, even when the switch is made to another probe port by a probe switching signal during operation of the system, the control circuitry 33 generates a clock signal corresponding to the position of the probe port to which the switch is made. Thus, no matter which of the probe ports is selected, it is possible to supply the probe port with a drive signal to drive the transmission circuitry 14 provided in the ultrasound probe 10 and a control signal to control the driving timing of the transmission circuitry 14 substantially in phase.

Accordingly, it is possible to suppress variation, among the probe ports, in delay difference between a drive signal that drives the transmission circuitry 14 provided in the ultrasound probe 10 and a control signal that controls the driving timing of the transmission circuitry 14.

According to the ultrasound diagnostic apparatus 1 of the first embodiment, the control circuitry 33 generates a control signal to be supplied to a designated probe port, on the basis of a correspondence relation in which a plurality of probe ports included in the apparatus main body 20 and a plurality of clock signals with different phases are associated with each other in accordance with the positions of the probe ports. It is thereby possible to easily realize suppression of variation, among the probe ports, in delay difference between a drive signal that drives the transmission circuitry 14 provided in the ultrasound probe 10 and a control signal that controls the driving timing of the transmission circuitry 14.

According to the ultrasound diagnostic apparatus 1 of the first embodiment, the correspondence relation represented by the control information is set in such a manner that a delay difference generated between a drive signal that drives the in-probe transmission circuitry 1421 and a control signal for the in-probe transmission circuitry 1421 falls within a predetermined range of values. It is thereby possible, when each probe port is used, to suppress, for example, variation in transmission phase and reception phase among the channels, and to suppress variation in transmission phase and reception phase among the transmission and reception rates.

According to the ultrasound diagnostic apparatus 1 of the first embodiment, the control circuitry 33 controls the multiplexer 32, and generates a clock signal corresponding to the position of the designated probe port. This eliminates the necessity to match the trace lengths of control signals connected to the respective probe ports among the probe ports, thus reducing the number of steps involved in designing the substrate of the ultrasound diagnostic apparatus, and reducing the size of the substrate.

In addition, the ultrasound diagnostic apparatus 1 according to the first embodiment comprises a frequency divider that frequency-divides a reference clock signal of a frequency higher than that of a control signal to be supplied to a probe port, and outputs a plurality of clock signals with different phases. This eliminates the necessity to provide a plurality of expensive oscillators.

Second Embodiment

In the first embodiment, a case has been described where the multiplexer 32 is provided in the apparatus main body 20, namely, a clock signal with a phase corresponding to a probe port to which the ultrasound probe is connected is selected in the apparatus main body 20. In the second embodiment, a case will be described where a multiplexer is provided in an ultrasound probe, namely, a clock signal with a phase corresponding to a probe port to which the ultrasound probe is connected is selected in the ultrasound probe.

An ultrasound diagnostic apparatus 1A according to the second embodiment will be described with reference to the block diagram shown in FIG. 7.

The ultrasound diagnostic apparatus 1A shown in FIG. 7 includes an ultrasound probe 10A and an apparatus main body 20A. The apparatus main body 20A is connected to an external apparatus 40 via a network 100. The apparatus main body 20A is connected to a monitor 50 and an input apparatus 60.

The ultrasound probe 10A includes, for example, a plurality of ultrasound transducers, a matching layer provided on the elements, and a backing material that prevents the ultrasound from propagating backward from the elements. The ultrasound probe 10A is detachably connected to the apparatus main body 20A. The ultrasound probe 10A according to the second embodiment is, for example, a two-dimensional array probe. Details of the ultrasound probe 10A will be described later.

The apparatus main body 20A is an apparatus that generates an ultrasound image based on a reflected wave signal received by the ultrasound probe 10A. As shown in FIG. 7, the apparatus main body 20A includes transmission circuitry 21, reception circuitry 22, signal processing circuitry 23, image generation circuitry 24, internal memory circuitry 25, an image memory (cine memory) 26, an image database 27, an input interface 28, a communication interface 29, an oscillator 30, a frequency divider 31A, control circuitry 33A, a switch 34, a switch 35, a switch 36, a probe port A, a probe port B, a probe port C, and a probe port D.

The oscillator 30 supplies a reference clock signal for driving the circuitry included in the apparatus main body 20A. The oscillator 30 generates a reference clock signal of, for example, 320 MHz, and supplies the generated reference clock signal to the frequency divider 31A.

The frequency divider 31A frequency-divides the reference clock signal supplied from the oscillator 30, and supplies the frequency-divided clock signal to the control circuitry 33A. For example, the frequency divider 31A frequency-divides a reference clock signal of 320 MHz supplied from the oscillator 30 by two, and supplies a clock signal of 160 MHz generated by the frequency division by 2 to the control circuitry 33A.

The control circuitry 33A is a processor that functions as, for example, the center of the ultrasound diagnostic apparatus 1. The control circuitry 33A executes a control program stored in the internal memory circuitry 25, thereby realizing a function corresponding to the program. Specifically, the control circuitry 33A includes a system control function 331. In the system control function 331, the control circuitry 33A supplies the clock signal generated by the frequency divider 31A to the ultrasound probe 10A via the probe port A, the probe port B, the probe port C, or the probe port D.

Next, the ultrasound probe 10A according to the second embodiment will be described with reference to FIG. 8. FIG. 8 is a block diagram showing an example of a configuration of the ultrasound probe 10A according to the second embodiment.

The ultrasound probe 10A includes a connecting member 11, a cable 12, and a probe main body 13A.

In FIG. 8, the probe main body 13A includes a plurality of transmission and reception ICs 14 and a plurality of ultrasound transducers 15. In addition, the probe main body 13A includes a frequency divider 16, a multiplexer 17, and control circuitry 18.

The frequency divider 16 generates a plurality of clock signals with different phases on the basis of, for example, a clock signal supplied from the apparatus main body 20A. The frequency divider 16 supplies the generated clock signals with different phases to the multiplexer 17. Specifically, the frequency divider 16 frequency-divides, for example, a clock signal of 160 MHz obtained by the frequency division by 2 by the frequency divider 31A included in the apparatus main body 20, and generates four clock signals of 80 MHz with different phases. The frequency divider 16 supplies the generated four clock signals to the multiplexer 17.

Of the four clock signals supplied from the frequency divider 16, the multiplexer 17 extracts one designated clock signal as a control signal to be supplied to the subarray unit 142 included in each of the transmission and reception ICs 14, under the control of the control circuitry 18. Thereby, control signals corresponding to the respective probe ports are generated. The multiplexer 17 supplies the generated control signals to the subarray units 142.

The control circuitry 18 is a processor that functions as, for example, the center of the ultrasound probe 10A. The control circuitry 18 executes a control program stored in memory circuitry (not shown in the drawings) included in the probe main body 13A, thereby realizing a function corresponding to the program. Specifically, the control circuitry 18 includes a clock control function 181.

The clock control function 181 is a function of generating control signals for in-probe transmission circuitry 1421 included in each transmission and reception IC 14 of the ultrasound probe 10A, according to the position of the probe port to which the ultrasound probe 10A is connected. When the clock control function 181 is executed, the control circuitry 18 selects a clock signal to be selected on the basis of the control information and the probe port to which the ultrasound probe 10A is connected. The information on the probe port to which the ultrasound probe 10A is connected is notified by the apparatus main body 20A, at the time of connection of the ultrasound probe 10A, or at the time of switching between the connections. The control circuitry 18 gives an instruction to the multiplexer 17 to extract the selected clock signal from, for example, four clock signals supplied from the frequency divider 16. Thereby, a clock signal corresponding to the position of the probe port to which the ultrasound probe 10A is connected is generated as a control signal in the multiplexer 17, and is supplied to the subarray unit 142 included in each of the transmission and reception ICs 14.

Let us assume that the control information is supplied from the internal memory circuitry 25 included in the apparatus main body 20A to the control circuitry 18, at the timing when the ultrasound probe 10A is connected to the apparatus main body 20A. The control information may be stored in a memory (not shown in the drawings) of the control circuitry 18. The control information may be generated by measuring a delay difference between the drive signal and the clock signal in the ultrasound probe 10A.

According to the second embodiment, the ultrasound probe 10A can be connected to the apparatus main body 20A including a plurality of probe ports. The ultrasound probe 10A includes in-probe transmission circuitry 1421 for driving ultrasound transducers 15 that generate ultrasound. The control circuitry 18 included in the ultrasound probe 10A generates a clock signal for the in-probe transmission circuitry 1421, according to the position of the probe port to which the ultrasound probe 10A is connected. It is thereby possible, as in the first embodiment in which the multiplexer 32 is provided in the apparatus main body 20, to suppress variation, among the probe ports, in delay difference between a drive signal that drives the transmission circuitry 14 provided in the ultrasound probe 10A and a control signal that controls the driving timing of the transmission circuitry 14.

Third Embodiment

In the first and second embodiments, cases have been described, as examples, where control signals corresponding to the probe ports to which the ultrasound probes 10 and 10A are connected are generated by the multiplexers 32 and 17. In the third embodiment, a case will be described where a drive signal corresponding to the probe port to which the ultrasound probe 10 is connected is generated.

Figure 9:
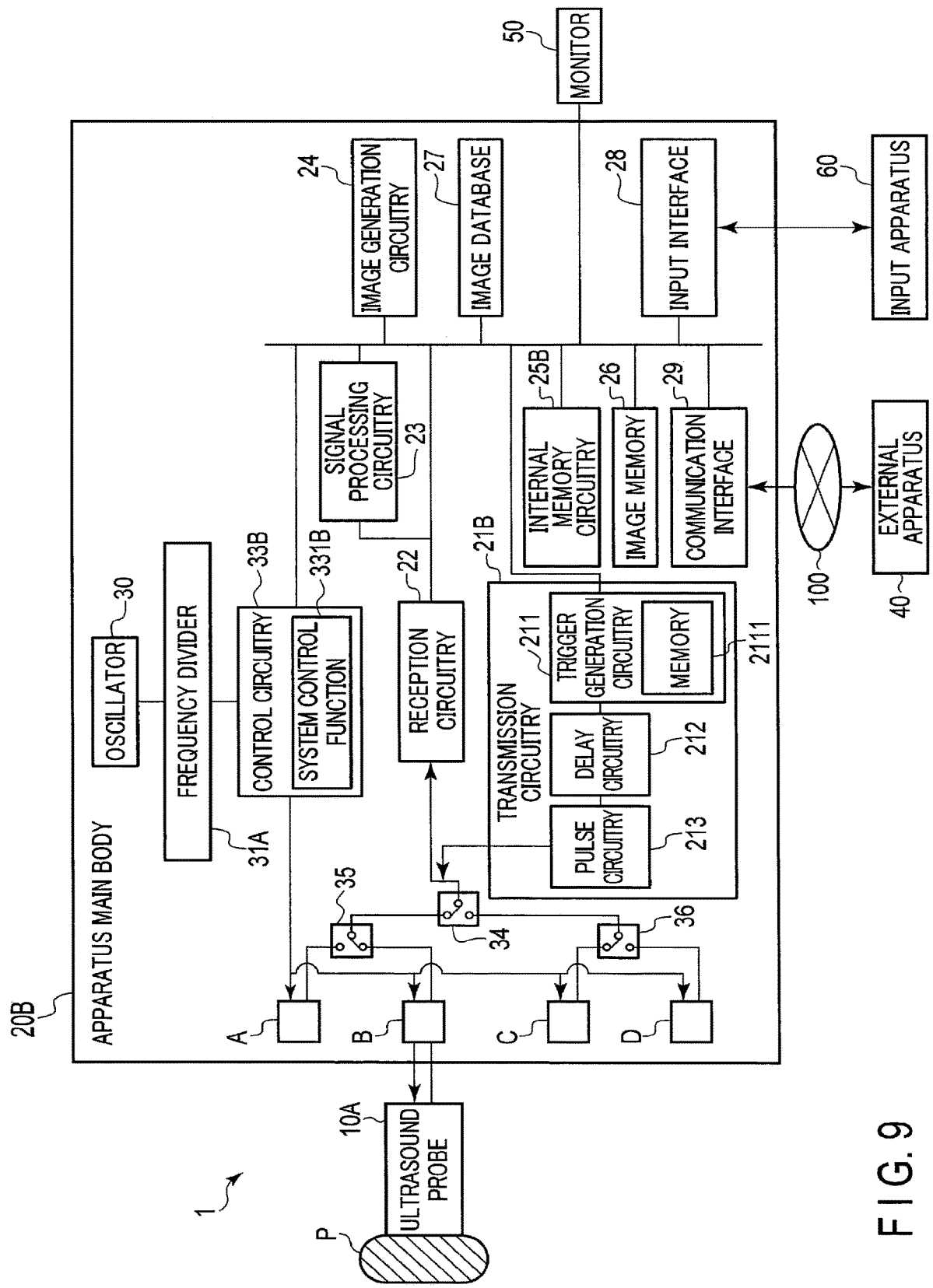
FIG. 9 is a diagram showing a configuration of an ultrasound diagnostic apparatus according to a third embodiment.

FIG. 9 is a block diagram showing a functional configuration of an ultrasound diagnostic apparatus 1B according to a third embodiment. The ultrasound diagnostic apparatus 1B shown in FIG. 9 includes an ultrasound probe 10 and an apparatus main body 20B.

The apparatus main body 20B is connected to an external apparatus 40 via a network 100. The apparatus main body 20B is connected to a monitor 50 and an input apparatus 60. The apparatus main body 20B is an apparatus that generates an ultrasound image based on a reflected wave signal received by the ultrasound probe 10.

As shown in FIG. 9, the apparatus main body 20B includes transmission circuitry 21B, reception circuitry 22, signal processing circuitry 23, image generation circuitry 24, internal memory circuitry 25B, an image memory (cine memory) 26, an image database 27, an input interface 28, a communication interface 29, an oscillator 30, a frequency divider 31A, control circuitry 33B, a switch 34, a switch 35, a switch 36, a probe port. A, a probe port B, a probe port C, and a probe port D.

The transmission circuitry 21B is a processor that supplies a drive signal (transmission pulse) corresponding to the position of the probe port to which the ultrasound probe 10 is connected to the ultrasound probe 10, under the control of the control circuitry 33B. The transmission circuitry 21B has a transmission control function of supplying drive signals to a plurality of ultrasound transducers 15 included in the ultrasound probe 10 via a plurality of channels.

The transmission control function of the transmission circuitry 21B is realized by, for example, a circuitry group provided for each channel. Specifically, the transmission circuitry 21B includes, for example, trigger generation circuitry 211, delay circuitry 212, and pulse circuitry 213, for each channel.

The trigger generation circuitry 211 includes, for example, a memory 2111. The memory 2111 stores, in advance, information for providing a phase difference to drive signals transmitted from the transmission circuitry 21B. The information for providing a phase difference to drive signals is, for example, a plurality of amounts of delay with different values. In the present embodiment, the memory 2111 stores, for example, four amounts of delay with different values, in advance. The trigger generation circuitry 211 provides a rate frequency based on a clock signal supplied from the control circuitry 33B with an amount of delay designated by the control circuitry 33B, of the amounts of delay stored in the memory 2111. The trigger generation circuitry 211 repeatedly generates rate pulses for forming transmission ultrasound at the delayed rate frequency.

The delay circuitry 212 provides each rate pulse generated by the trigger generation circuitry 211 with a transmission delay time for each element. The pulse circuitry 213 generates a drive signal at a timing based on the rate pulse, and supplies the generated drive signal to the ultrasound probe 10. Thereby, drive signals with different phases are output from the transmission circuitry 21B, according to the probe port to which the ultrasound probe 10 is connected.

Figure 10:
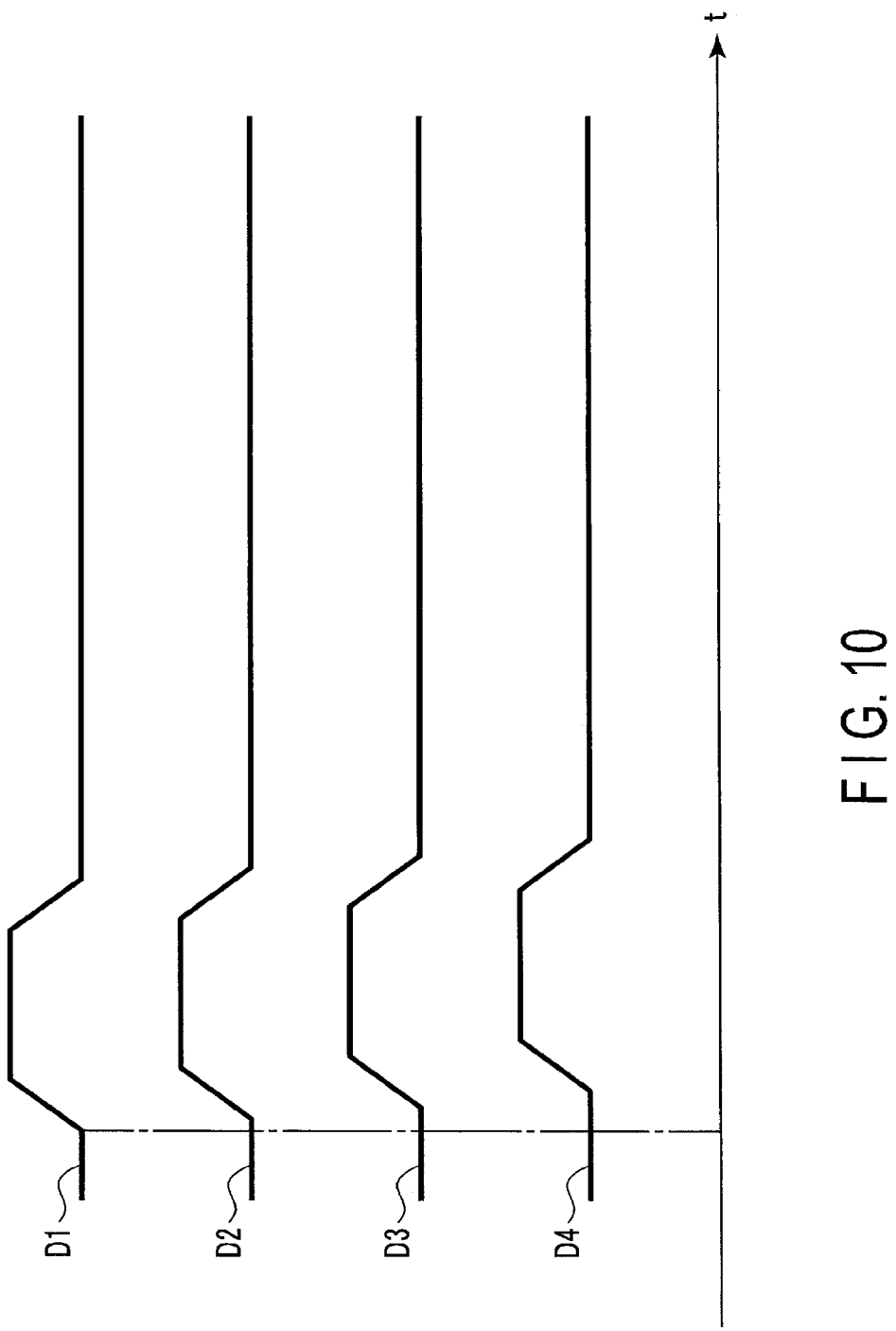
FIG. 10 is a diagram showing drive signals that may be output from transmission circuitry shown in FIG. 9.

FIG. 10 is a schematic diagram showing an example of four drive signals with different phases that may be output from the transmission circuitry 21B shown in FIG. 9. Even though the drive signals are not simultaneously generated, they are shown in tandem in FIG. 10 to indicate the phase differences. One of the drive signals D1 to D4 shown in FIG. 10 is supplied to the ultrasound probe 10.

The selected amount of delay is not limited to the one that is supplied by the trigger generation circuitry 211. The selected amount of delay may be realized in other ways, where drive signals with different phases are output from the transmission circuitry 21B, according to the probe port to which the ultrasound probe 10 is connected. For example, the selected amount of delay may be supplied by the delay circuitry 212 or the pulse circuitry 213.

The internal memory circuitry 25B stores a control program, etc. relating to a method for setting an amount of delay according to the third embodiment. The internal memory circuitry 25B stores control information. The control information according to the third embodiment is information for controlling, for example, a drive signal. In the control information, a plurality of probe ports included in the apparatus main body 20B and information for generating a plurality of drive signals with different phases are associated with each other in accordance with the positions of the probe ports. At this time, the information associated with the probe ports is information stored in the memory 2111, e.g., amounts of delay with different values. In this correspondence relation, a probe port and an amount of delay are associated in such a manner that a delay difference generated between a drive signal input to the in-probe transmission circuitry 1421 in the ultrasound probe 10 connected to the probe port and a clock signal input to the in-probe transmission circuitry 1421 falls within a predetermined range of values.

The control information may be stored in a flash memory, for example, implemented on the control circuitry 33B, and read at the time of activation of the apparatus. The control information may be updated as necessary via, for example, the input interface 28.

The control circuitry 33B is a processor that functions as, for example, the center of the ultrasound diagnostic apparatus 1B. The control circuitry 33B executes the control program stored in the internal memory circuitry 25B, thereby realizing a function corresponding to the operating program. Specifically, the control circuitry 33B includes a system control function 331B.

The system control function 331B is a function of controlling basic operations of the ultrasound diagnostic apparatus 1B, such as input and output, and transmission and reception of the ultrasound. When the system control function 331B is executed, the control circuitry 33B performs various types of control, using, for example, a clock based on a clock signal supplied from the frequency divider 31A as a reference clock. For example, the control circuitry 33B controls the timing of transmission, and transfers setting data to the circuitry, using a clock based on a clock signal of 160 MHz supplied from the frequency divider 31A as a reference clock.

The control circuitry 33B reads control information from the internal memory circuitry 25B. The control circuitry 33B acquires a setting value corresponding to the designated probe port, on the basis of the read control information. The control circuitry 33B gives an instruction to the transmission circuitry 21B to select the acquired setting value (amount of delay) from, for example, the four amounts of delay stored in the memory 2111. Thereby, rate pulses are generated from, for example, the trigger generation circuitry 211 of the transmission circuitry 21B, at a rate frequency supplied by the amount of delay corresponding to the designated probe port.

The control circuitry 33B computes delay control data (delay data) on a delay time (a transmission delay time and a reception delay time) set in each of the ultrasound transducers at the time of transmission and reception of the ultrasound. The control circuitry 33B supplies the computed delay data to the ultrasound probe 10, together with the setting information.

Next, the operation from start of ultrasound scanning until provision of a drive signal and a clock signal to the in-probe transmission circuitry 1421 will be described. In the description that follows, let us assume that ultrasound probes are connected to the respective probe ports A, B, C, and D. The ultrasound probes connected to the respective probe ports A, B, C, and D have configurations similar to that of the ultrasound probe 10 shown in FIG. 3; however, let us assume that their shapes and structures, and some of their functions vary depending on the intended use.

Upon receiving an instruction to start ultrasound scanning via, for example, the input interface 28, the control circuitry 33B included in the apparatus main body 20B executes the system control function 331B, and reads control information from the internal memory circuitry 25B. At this time, the control information represents, for example, a correspondence relation between the probe ports A, B, C, and D and four amounts of delay with different values.

In this correspondence relation, the probe ports A, B, C, and D and the four amounts of delay are associated with each other in such a manner that drive signals that drive the in-probe transmission circuitry 1421 and clock signals that control the driving timing of the in-probe transmission circuitry 1421 are substantially synchronized, when observed with an oscilloscope by the operator.

The control circuitry 33B acquires an amount of delay corresponding to the designated probe port, on the basis of the read control information. The control circuitry 33B gives an instruction to the transmission circuitry 21B to select the acquired amount of delay. The control circuitry 33B supplies the transmission circuitry 21B with a clock signal of 160 MHz generated in the frequency divider 31A. Thereby, the drive signal delayed by the selected amount of delay is supplied from the transmission circuitry 21B to the in-probe transmission circuitry 1421 via the designated probe port.

The control circuitry 33B supplies a clock signal of, for example, 80 MHz generated by the frequency divider 31A to the ultrasound probe 10 via the probe port A, the probe port B, the probe port C, or the probe port D.

Upon receiving an instruction to switch to another probe port via, for example, the input interface 28 after the start of ultrasound scanning, the control circuitry 33B acquires a setting value corresponding to the probe port to which the switch is made, on the basis of the control information read at the time of start of the ultrasound scanning. The control circuitry 33B gives an instruction to the transmission circuitry 21B to select the acquired setting value. Thereby, after the switch is made to another probe port, namely, after the switch is made to an ultrasound probe to be used, a drive signal supplied with an amount of delay corresponding to the position of the probe port to which the switch is made is output from the transmission circuitry 21B. The output drive signal is supplied to the in-probe transmission circuitry 1421 of a corresponding channel, via the probe port to which the switch is made.

According to the third embodiment, the apparatus main body 20B of the ultrasound diagnostic apparatus 1B includes probe ports A, B, C, and D, to which an ultrasound probe 10 including an in-probe transmission circuitry 1421 for driving transducers that generate ultrasound can be connected. The control circuitry 33B included in the apparatus main body 20B controls the transmission circuitry 21B, and generates a drive signal for the in-probe transmission circuitry 1421 provided in the ultrasound probe 10, according to the position of the probe port to which the ultrasound probe 10 is connected.

It is thereby possible to perform ultrasound scanning while minimizing the delay difference between a drive signal that drives the in-probe transmission circuitry 1421 provided in the ultrasound probe 10 and a control signal that controls the driving timing of the in-probe transmission circuitry 1421, no matter which of the probe ports is used.

Various types of signals input to the in-probe transmission circuitry 1421 via the probe ports in the ultrasound diagnostic apparatus 1B according to the third embodiment may be described with reference to FIG. 5. It can be seen, from FIG. 5, that the timing when a clock signal reaches a probe port varies among the probe ports, according to the distance between the transmission circuitry 21B and the probe port. On the other hand, each probe port is supplied with a drive signal that is delayed according to the position of the probe port. Thus, the rising edge timing of a drive signal and the ON-to-OFF transition timing of a clock signal are substantially aligned in each of the probe ports. That is, the drive signal and the clock signal are substantially synchronized. This suppresses the variation in delay difference between the clock signal supplied to the in-probe transmission circuitry 1421 via the probe ports A, B, C, and D and the drive signal supplied from the transmission circuitry 21B to the in-probe transmission circuitry 1421 via the probe ports A, B, C, and D.

According to the ultrasound diagnostic apparatus 1B of the third embodiment, the control circuitry 33B generates a drive signal to be supplied to a designated probe port on the basis of a correspondence relation in which a plurality of probe ports included in the apparatus main body 20B and information for providing a phase difference to the drive signals are associated with each other in accordance with the positions of the probe ports. It is thereby possible to easily realize suppression of variation, among the probe ports, in delay difference between a drive signal that drives the transmission circuitry 14 provided in the ultrasound probe 10 and a control signal that controls the driving timing of the transmission circuitry 14.

According to the ultrasound diagnostic apparatus 1B of the third embodiment, the correspondence relation represented by the control information is set in such a manner that a delay difference generated between a drive signal that drives the in-probe transmission circuitry 1421 and control signal for the in-probe transmission circuitry 1421 falls within a predetermined range of values. It is thereby possible, when each probe port is used, to suppress, for example, variation in transmission phase and reception phase among the channels, and to suppress variation in transmission phase and reception phase among the transmission and reception rates.

According to the ultrasound diagnostic apparatus 1B of the third embodiment, the control circuitry 33B controls the transmission circuitry 21B, and generates a drive signal corresponding to the position of the designated probe port. This eliminates the necessity to match the trace lengths of drive signals connected to the respective probe ports among the probe ports, thus reducing the number of steps involved in designing the substrate of the ultrasound diagnostic apparatus, and reducing the size of the substrate.

Fourth Embodiment

In the third embodiment, a case has been described where drive signals with different phases are generated in the transmission circuitry 21B of the apparatus main body 20B, according to the position of the probe port to which the ultrasound probe 10 is connected. In the fourth embodiment, a case will be described where a delay is provided to a drive signal in an ultrasound probe.

Figure 11:
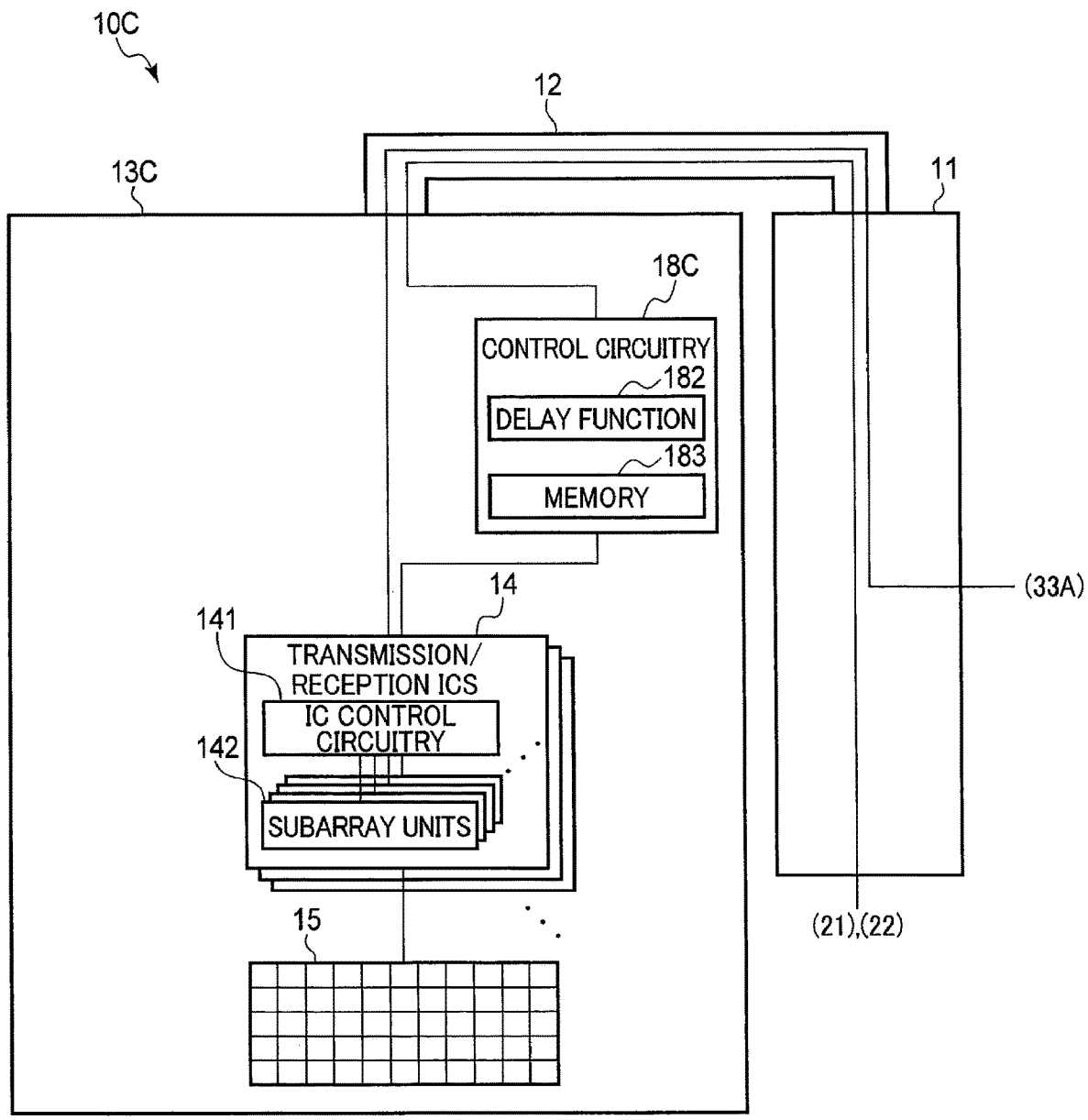
FIG. 11 is a view showing a configuration of an ultrasound probe according to a fourth embodiment.

FIG. 11 is a block diagram showing an example of a functional configuration of an ultrasound diagnostic apparatus 1C according to the fourth embodiment.

The ultrasound diagnostic apparatus 1C shown in FIG. 11 includes an ultrasound probe 10C and an apparatus main body 20A.

The ultrasound probe 10C includes a plurality of ultrasound transducers, a matching layer provided on the elements, and a backing material that prevents the ultrasound from propagating backward from the elements. The ultrasound probe 10C is detachably connected to the apparatus main body 20A. The ultrasound probe 10C according to the fourth embodiment is, for example, a two-dimensional array probe. The ultrasound probe 10C includes, for example, a connecting member 11, a cable 12, and a probe main body 13C.

The probe main body 13C includes control circuitry 18C, a plurality of transmission and reception ICs 14 and a plurality of ultrasound transducers 15.

The control circuitry 18C generates drive signals to drive the transmission and reception ICs 14 on the basis of drive signals supplied from, for example, the apparatus main body 20A. The control circuitry 18C supplies the generated drive signals to the transmission and reception ICs 14.

The control circuitry 18C realizes a delay function 182 by, for example, executing a control program stored in memory circuitry (not shown in the drawings) included in the probe main body 13C. The delay function 182 is a function of delaying a drive signal supplied from the apparatus main body 20A, according to the probe port to which the ultrasound probe 10C is connected.

Specifically, the control circuitry 18C includes, for example, a memory 183. The memory 183 stores, in advance, information for providing a phase difference to drive signals supplied from the apparatus main body 20A. The information for providing a phase difference to drive signals is, for example, a plurality of amounts of delay with different values. In the fourth embodiment, let us assume that the memory 183 stores, for example, four amounts of delay with different values, in advance.

In the delay function 182, the control circuitry 18C selects, from the memory 183, an amount of delay corresponding to the probe port to which the ultrasound probe 10C is connected, on the basis of the control information described in the third embodiment. The control information may be read from the internal memory circuitry 25 of the apparatus main body 20A, or stored in a memory 183 of the control circuitry 18C. The information on the probe port to which the ultrasound probe 10C is connected is notified by, for example, the apparatus main body 20A at the time of connection of the ultrasound probe 10C, or at the time of switching between the connections. The control circuitry 18C delays a drive signal supplied from the apparatus main body 20A by a selected amount of delay. The control circuitry 18C supplies the delayed drive signal to a subarray unit 142.

According to the fourth embodiment, the ultrasound probe 10C can be connected to the apparatus main body 20A including a plurality of probe ports. The ultrasound probe 10C includes in-probe transmission circuitry 1421 for driving ultrasound transducers 15 that generate ultrasound. The control circuitry 18C included in the ultrasound probe 10C generates drive signals for the in-probe transmission circuitry 1421, according to the position of the probe port to which the ultrasound probe 10C is connected. It is thereby possible to suppress variation, among the probe ports, in delay difference between a drive signal that drives the transmission circuitry 14 provided in the ultrasound probe 10C and a control signal that controls the driving timing of the transmission circuitry 14.

The term "processor" used in the above explanation refers to, for example, circuitry such as a central processing unit (CPU), a graphics processing unit (GPU), an ASIC, a programmable logic device (e.g., an SPLD, a CPLD, or an FPGA), etc. The processor reads and executes programs stored in memory circuitry to execute the respective functions. The programs may be incorporated in circuitry of the processor, instead of storing them in the memory circuitry. In this case, the processor reads the programs incorporated in its circuitry and executes them to realize the respective functions. The processors described in connection with the above embodiments are not limited to single-circuit processors. A plurality of independent processors may be combined and integrated as one processor with such functions. Furthermore, a plurality of structural elements of the above embodiments may be integrated into one processor with such functions.

According to at least one of the embodiments described above, it is possible to suppress variation, among the probe ports, in delay difference between a drive signal that drives the transmission circuitry provided in the ultrasound probe and a control signal that controls the driving timing of the transmission circuitry by the driving signal.

While certain embodiments have been described, these embodiments have been presented by way of example only, and are not intended to limit the scope. Indeed, the novel embodiments described herein may be embodied in a variety of other forms; furthermore, various omissions, substitutions and changes in the form of the embodiments described herein may be made without departing from the spirit. The accompanying claims and their equivalents are intended to cover such forms or modifications as would fall within the scope and spirit.

The invention claimed is:

1. An ultrasound diagnostic apparatus comprising:
an ultrasound probe including transmission circuitry to drive transducers that generate ultrasound;
a plurality of probe ports to which the ultrasound probe is connectible;
processing circuitry that generates a control signal for the transmission circuitry or a drive signal to drive the transmission circuitry, according to a position of one of the probe ports to which the ultrasound probe is connected.

2. The ultrasound diagnostic apparatus according to claim 1, wherein
the processing circuitry generates the control signal based on a correspondence relation in which the probe ports are associated with a plurality of clock signals with different phases in accordance with respective positions of the probe ports.

3. The ultrasound diagnostic apparatus according to claim 2, wherein
the correspondence relation is set in such a manner that a delay difference generated between a drive signal to drive the transmission circuitry and the control signal falls within a predetermined range of values.

4. The ultrasound diagnostic apparatus according to claim 2, further comprising:
a multiplexer that outputs one of the clock signals, wherein
the processing circuitry generates the control signal by selecting, based on the correspondence relation, a clock signal corresponding to the position of each of the probe ports, and causing the multiplexer to output the selected clock signal.

5. The ultrasound diagnostic apparatus according to claim 2, further comprising:
a frequency divider that frequency-divides a reference clock signal having a frequency higher than the control signal, and that outputs the clock signals.

6. The ultrasound diagnostic apparatus according to claim 1, wherein
the processing circuitry generates the drive signal based on a correspondence relation in which the probe ports are associated with information to generate a plurality of drive signals with different phases, in accordance with the respective positions of the probe ports.

7. The ultrasound diagnostic apparatus according to claim 6, wherein
the correspondence relation is set in such a manner that a delay difference generated between the drive signal and a control signal for the transmission circuitry falls within a predetermined range of values.

8. The ultrasound diagnostic apparatus according to claim 6, wherein
the processing circuitry generates the drive signal by selecting, based on the correspondence relation, information corresponding to the position of each of the probe ports, and using the selected information.

* * * * *